United States Patent
Moroni et al.

(10) Patent No.: US 6,620,426 B2
(45) Date of Patent: Sep. 16, 2003

(54) TABLET COATING COMPOSITION

(75) Inventors: Antonio Moroni, Morris Plains, NJ (US); Nadhamuni G. Nerella, Bridgewater, NJ (US); William Drefko, Kearny, NJ (US)

(73) Assignee: ISP Investments Inc., Wilmington, DE (US)

( * ) Notice: Subject to any disclaimer, the term of this patent is extended or adjusted under 35 U.S.C. 154(b) by 138 days.

(21) Appl. No.: 09/875,511

(22) Filed: Jun. 5, 2001

(65) Prior Publication Data

US 2002/0192284 A1 Dec. 19, 2002

(51) Int. Cl.[7] .............................................. A61K 47/00
(52) U.S. Cl. ........................ 424/439; 424/400; 424/464; 424/474; 424/489; 424/490
(58) Field of Search ............................. 424/400, 439, 424/464, 474, 489, 490

(56) References Cited

U.S. PATENT DOCUMENTS 5,641,513 A * 6/1997 Lech et al. ................. 424/468
6,326,028 B1 * 12/2001 Nivaggioli et al. ......... 424/474

* cited by examiner

Primary Examiner—Thurman K. Page
Assistant Examiner—Charesse Evans
(74) Attorney, Agent, or Firm—Walter Katz; William J. Davis; Marilyn J. Maue

(57) ABSTRACT

A tablet coating composition including a mixture of (a) sodium alginate and (b) a polyvinylpyrrolidone-vinyl acetate copolymer, and, optionally, (c) hydroxypropylmethyl cellulose, and/or hydroxypropyl cellulose.

6 Claims, No Drawings

TABLET COATING COMPOSITION

BACKGROUND OF THE INVENTION

1. Field of the Invention

This invention relates to tablet coating compositions, and, more particularly, to such composition having an advantageous combination of physical properties which is a mixture in predetermined proportions of sodium alginate and a polyvinylpyrrolidone-vinyl acetate copolymer.

2. Description of the Prior Art

Hydroxymethyl cellulose is a good film former; however, its films are brittle, opaque and non-slippery. Accordingly, it is desired to provide new and improved tablet coating compositions.

SUMMARY OF THE INVENTION

What is described herein is a tablet coating composition which includes a mixture of (a) sodium alginate and (b) a polyvinylpyrrolidone-vinyl acetate copolymer, and, optionally, (c) hydroxypropylmethyl cellulose, and/or hydroxypropyl cellulose.

This composition provides the tablet with a predetermined degree of luster, strength, smoothness, slipperiness, color, modified release and ease of polishing.

In the preferred form of the invention, composition (b) includes by weight, 60–80% vinylpyrrolidone and 20–40% vinyl acetate; preferably the composition has a K-value of about 25 to 34, calculated from its kinematic viscosity on a 1% aqueous solution.

Most preferably, the composition comprises, by weight, (a) 10–98%, (b) 2–20%, and (c) 0–88%.

Application formulations of the composition of the invention include a medicament, and/or a nutritional supplements.

DETAILED DESCRIPTION OF THE INVENTION

In this invention, tablets are coated with a predetermined mixture of (a) sodium alginate and (b) a polyvinylpyrrolidone-vinyl acetate copolymer, (Plasdone® S-630, International Specialty Products, Inc.), optionally with hydroxypropylmethyl cellulose, and/or hydroxypropyl cellulose.

Experimental

1. Process/Composition:

Aqueous solutions of sodium alginates (Manucol LD, 5 cps or Keltone LV, 50 cps), and Plasdone® S-630, and color lakes, were sprayed onto placebo tablets* in a Glatt fluid-bed Wurster coater. The coated tablets were characterized by their weight gain, and, subjectively, for coating uniformity, lustrousness, and slipperiness/tackiness when exposed to aqueous fluids.

* Placebo (lactose) tablets from Korsch Processing laboratory were convex tablets (7.5 mm diameter; average thickness 5.6 mm), and the average tablet weight was 201.3 mg.

2. Fluid Bed Conditions:

Glatt fluid-bed coater with Wurster adapter and plate B.

Batch size 400 g.

Spray rate: 10 g/min

Atomization pressure: 3 bar.

Drying air temperature: 60° C.

Flap: 35% open.

3. Coating Procedure and Results:

Examples 1 and 2 were solutions of 10% Manucol LD with and without 2% by weight of Plasdone® S-630; 1000 ml of each were sprayed onto 400 g placebo tablets. The presence of the S-630 polymer in the mixture gave the coated tablets a superior feeling of slipperiness.

Examples 2 and 4 were prepared similarly as in Examples 1 and 2; however, with the addition of 0.5% Yellow lake to allow for better evaluation of coating uniformity. An increase in luster was observed in S-630 containing coated tablets.

Examples 5 and 6 were prepared with Keltone LV with and without S-630. These solutions were prepared with Keltone LV at a concentration of 5.43% to maintain the viscosity of the solution at an acceptable level, and with 0.36% Red lake. Tablets coated with the Keltone/S-630 solution gave a lustrous, slippery coating when wet. Tablets coated with Keltone only produced an uneven coating, which was unacceptable, and tackiness, rather than slipperiness, when wet.

TABLE

| Ex. No. | Alginate, (%) | Plasdone ® S-630 (%) | Lake, (%) | Wt. Increase (%) | Physical Properties of Coating |
|---|---|---|---|---|---|
| 1 | Manucol LD, 10 | 2 | — | 3.00 | Lustrous, slippery coating |
| 2 | Manucol LD, 10 | — | — | 3.52 | Lustrous, tacky then slippery coating |
| 3 | Manucol LD, 10 | 2 | Yellow, 0.5 | 3.93 | Lustrous, slippery coating |
| 4 | Manucol LD, 10 | — | Yellow, 0.5 | 3.27 | Borderline lustrous, slippery coating |
| 5 | Keltone LV, 5.43 | 0.72 | Red, 0.36 | 7.05 | Lustrous, slippery coating |
| 6 | Keltone LV, 5.43 | — | Red, 0.36 | 2.19 | Uneven coating, tacky |

*K-value = 25–34, as calculated from kinematic viscosity on 1% aqueous solution.

The results show that aqueous solutions of the tablet coating compositions of the invention comprising: (a) sodium alginate and (b) polyvinyl pyrrolidone (PVP)-vinyl acetate (VA) copolymer (Plasdone® S-630, 60% PVP, 30% VA, by wt.) have a lowered viscosity* where it makes them easy to spray, even at a solids contents of 20%. These compositions produce a superior coating when compared to each of the ingredients alone. If desired, (c) hydroxymethyl cellulose may be included in the composition in suitable amounts. Application formulations of the composition also may include a medicament and/or nutritional supplement.

* K-value=25–34, as calculated from kinematic viscosity on 1% aqueous solution.

While the invention has been described with particular reference to certain embodiments thereof, it will be understood that changes and modifications may be made which are within the skill of the art. Accordingly, it is intended to be bound only by the following claims, in which:

What is claimed is:

1. A tablet coating composition comprising a mixture of, by weight, (a) 10–98% sodium alginate, and (b) 2–20% polyvinylpyrrolidone-vinyl acetate copolymer, and, optionally, (c) 0–88% hydroxypropylmethyl cellulose hydroxypropyl cellulose.

2. A composition according to claim 1 wherein (b) comprises, by weight, 60–80% vinylpyrrolidone and 20–40% vinyl acetate, and said composition has a K-value of about 25 to 34, calculated from its kinematic viscosity on a 1% aqueous solution.

3. A composition according to claim 1 including a medicament and/or a nutritional supplement.

4. A tablet coating solution comprising the tablet coating composition of claims 1, 2 or 3 and a solvent.

5. A solution according to claim 4 wherein the solvent is water.

6. A tablet coated uniformly with the solution of claim 4.

* * * * *